(12) United States Patent
Donde et al.

(10) Patent No.: US 9,000,032 B2
(45) Date of Patent: Apr. 7, 2015

(54) SUBSTITUTED CYCLOPENTENES AS THERAPEUTIC AGENTS

(71) Applicant: Allergan, Inc., Irvine, CA (US)

(72) Inventors: Yariv Donde, Dana Point, CA (US); Jeremiah H. Nguyen, La Puente, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/291,416

(22) Filed: May 30, 2014

(65) Prior Publication Data

US 2014/0357705 A1 Dec. 4, 2014

Related U.S. Application Data

(60) Provisional application No. 61/835,059, filed on Jun. 14, 2013, provisional application No. 61/829,892, filed on May 31, 2013.

(51) Int. Cl.
*A61K 31/381* (2006.01)
*C07D 333/38* (2006.01)

(52) U.S. Cl.
CPC .................................. *C07D 333/38* (2013.01)

(58) Field of Classification Search
USPC ............................................ 549/71; 514/448
See application file for complete search history.

(56) References Cited

U.S. PATENT DOCUMENTS

| | | | |
|---|---|---|---|
| 4,066,834 | A | 1/1978 | Woessner et al. |
| 4,166,452 | A | 9/1979 | Generales, Jr. |
| 4,256,108 | A | 3/1981 | Theeuwes |
| 4,265,874 | A | 5/1981 | Bonsen et al. |
| 7,091,231 | B2 | 8/2006 | Donde et al. |
| 7,427,685 | B2 | 9/2008 | Donde et al. |
| 7,439,372 | B2 | 10/2008 | Yariv et al. |
| 7,713,968 | B2 | 5/2010 | Donde et al. |
| 8,722,726 | B2* | 5/2014 | Donde et al. .................. 514/448 |

FOREIGN PATENT DOCUMENTS

| | | |
|---|---|---|
| WO | WO9517393 | 6/1995 |
| WO | WO9519964 | 7/1995 |
| WO | WO9855468 | 12/1998 |
| WO | WO9926629 | 6/1999 |
| WO | WO0016760 | 3/2000 |
| WO | WO2007115020 A2 | 10/2007 |

OTHER PUBLICATIONS

Yoshitaka, Uji, Drug Treatment of Glaucoma, Frontiers in Glaucoma, 2006, p. 26(144)-33(151). (Complete Translation), vol. 7, No. 3.
Carey, Francis A., Organic Chemistry, New York: McGraw-Hill Book Company, 1987, p. 63.
Silverman, Richard B., Organic Chemistry of Drug Design and Drug Action, 2nd Edition, Elsevier Academic Press: Amsterdam, 2004, p. 497-557.
Remingtons Pharmaceutical Sciences, Mack Publishing Company, Easton, PA., 16th Edition, 1980.

* cited by examiner

*Primary Examiner* — Kristin Vajda
(74) *Attorney, Agent, or Firm* — Jonathan Y. Bass

(57) ABSTRACT

Disclosed herein are compounds having a formula:

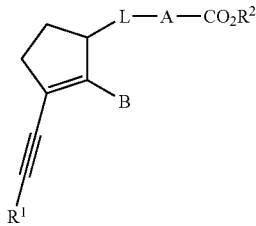

or a pharmaceutically acceptable salt thereof, as well as therapeutic methods, medicaments, and compositions related thereto.

16 Claims, No Drawings

SUBSTITUTED CYCLOPENTENES AS THERAPEUTIC AGENTS

CROSS-REFERENCE TO RELATED APPLICATIONS

This application is a non-provisional application claiming the benefit of U.S. provisional application 61/829,892 filed on May 31, 2013, and U.S. provisional application 61/835,059 filed on Jun. 14, 2013, each of which is incorporated by reference in their entirety and serve as the basis for a priority claim of the present application.

FIELD

The present invention relates generally to compounds and methods for treating ocular disorders. The invention relates in particular to the use of certain well-defined substituted cyclopentenes for the treatment of ocular hypertension and glaucoma.

BACKGROUND

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

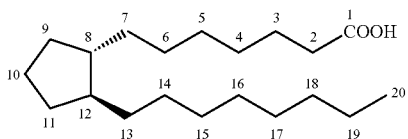

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\alpha}$)].

Therefore, there is a need for compounds for treating glaucoma or ocular hypertension, such as the substituted cyclopentenes described herein.

SUMMARY

The invention provides well defined substituted cyclopentenes for treating glaucoma or ocular hypertension.

In a first aspect, some embodiments include compounds having the structure:

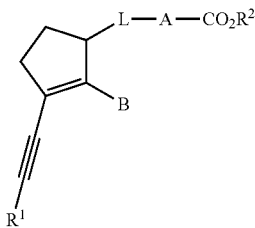

wherein:
L is $C_1$-$C_6$ alkylene;
A is arylene or heteroarylene;
B is substituted or unsubstituted aryl;
$R^1$ is H, $C_1$-$C_6$ alkyl, —$CH_2OH$, —$CF_3$, aryl, or heteroaryl; and
$R^2$ is H, $C_1$-$C_6$ alkyl, hydroxyethyl,

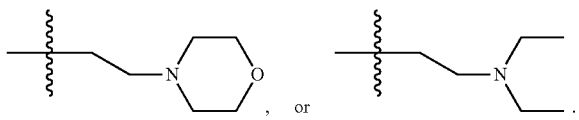

In a second aspect, some embodiments include compositions including at least one compound described herein and at least one pharmaceutically acceptable excipient, wherein the composition is a liquid which is ophthalmically acceptable.

In a third aspect, some embodiments include methods for treating glaucoma or ocular hypertension. Such methods can be performed, for example, by administering to a subject in need thereof a compound of the invention.

In a fourth aspect, some embodiments include kits including at least one composition described herein, a container, and instructions for administration of the composition to a subject in need thereof for the treatment of glaucoma or ocular hypertension.

DETAILED DESCRIPTION

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting. The section headings used herein are for organizational purposes only and are not to be construed as limiting the subject matter described.

Unless specific definitions are provided, the nomenclatures utilized in connection with the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning. Standard techniques can be used for chemical syntheses, chemical analyses, and formulation.

As used herein, "alkyl" refers to straight or branched chain hydrocarbyl groups having from 1 up to about 100 carbon atoms. Whenever it appears herein, a numerical range, such as "1 to 100" or "$C_1$-$C_{100}$", refers to each integer in the given range; e.g., "$C_1$-$C_{100}$ alkyl" means that an alkyl group may comprise only 1 carbon atom, 2 carbon atoms, 3 carbon atoms, etc., up to and including 100 carbon atoms, although the term "alkyl" also includes instances where no numerical range of carbon atoms is designated. For example, the term "alkyl" can refer to a sub-range between $C_1$-$C_{100}$ (e.g. $C_1$-$C_6$). "Substituted alkyl" refers to alkyl moieties bearing substituents including alkyl, alkenyl, alkynyl, hydroxy, oxy, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, haloalkyl, cyano, nitro, nitrone, amino, lower alkylamino, lower alkyldiamino, amido, azido, —C(O)H, —C(O)$R_7$, —CH$_2$O$R_7$, —C(O)O—, —C(O)—, —S—, —S(O)$_2$—, —OC(O)O—, wherein $R_7$ is H or lower alkyl, acyl, oxyacyl, carboxyl, carbamate, sulfonyl, sulfonamide, sulfuryl, and the like. As used herein, "lower alkyl" refers to alkyl moieties having from 1 to about 6 carbon atoms.

As used herein, the term "alkylene" refers to a divalent alkyl moiety, meaning the alkylene moiety is attached to the rest of the molecule at both ends of the alkyl unit. Exemplary alkylenes include, for example, —CH$_2$— (methylene), —(CH$_2$)$_2$— (ethylene), —(CH$_2$)$_3$— (propylene), —(CH$_2$)$_4$— (butylene), and others that would be apparent to a skilled person.

As used herein, "alkenyl" refers to straight or branched chain hydrocarbyl groups having at least one carbon-carbon double bond, and having in the range of about 2 up to about 100 carbon atoms, and "substituted alkenyl" refers to alkenyl groups further bearing one or more substituents as set forth above. As used herein, "lower alkenyl" refers to alkenyl moieties having from 2 to about 6 carbon atoms.

As used herein, the term "alkenylene" refers to a divalent alkenyl moiety, meaning the alkenylene moiety is attached to the rest of the molecule at two positions.

As used herein, "alkynyl" refers to straight or branched chain hydrocarbyl groups having at least one carbon-carbon triple bond, and having in the range of about 2 up to about 100 carbon atoms, and "substituted alkynyl" refers to alkynyl groups further bearing one or more substituents as set forth above. As used herein, "lower alkynyl" refers to alkynyl moieties having from 2 to about 6 carbon atoms.

As used herein, "cycloalkyl" refers to cyclic (i.e., ring-containing) alkyl moieties typically containing in the range of about 3 up to about 8 carbon atoms, and "substituted cycloalkyl" refers to cycloalkyl groups further bearing one or more substituents as set forth above. "Cycloalkyl" also refers to bicyclic moieties, such as norbornyl, and the like.

As used herein, "cycloalkenyl" refers to cyclic (i.e., ring-containing) alkenyl moieties typically containing in the range of about 3 up to about 8 carbon atoms, and "substituted cycloalkenyl" refers to cycloalkenyl groups further bearing one or more substituents as set forth above. "Cycloalkenyl" also refers to bicyclic moieties, such as norbornenyl, and the like.

As used herein, "aryl" refers to aromatic groups having in the range of 5 up to 14 carbon atoms and "substituted aryl" refers to aryl groups further bearing one or more substituents as set forth above.

As used herein, "heteroaryl" refers to aromatic moieties containing one or more heteroatoms (e.g., N, O, S, or the like) as part of the ring structure and having in the range of 5 up to 14 total atoms in the ring structure (i.e., carbon atoms and heteroatoms). "Substituted heterocyclic" refers to heterocyclic groups further bearing one or more substituents as set forth above.

As used herein "arylene" or "heteroarylene" refers to an aryl ring or ring system or a heteroaryl ring or ring system which connects two other parts of a molecule, i.e. the two parts are bonded to the ring in two distinct ring positions. Arylene or heteroarylene may be substituted or unsubstituted. Unsubstituted arylene or heteroarylene has no substituents other than the two parts of the molecule it connects. Substituted arylene or heteroarylene has substituents in addition to the two parts of the molecule it connects. Exemplary arylenes and heteroarylenes include, for example:

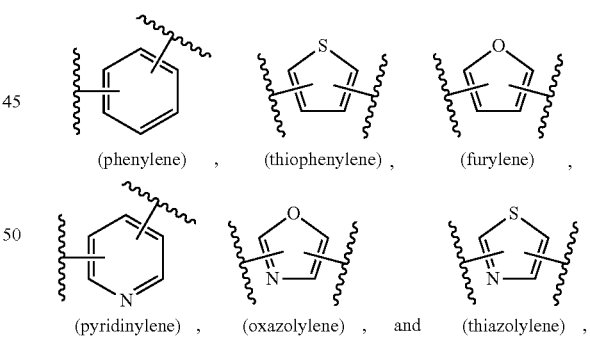

(phenylene), (thiophenylene), (furylene), (pyridinylene), (oxazolylene), and (thiazolylene), where

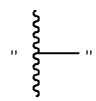

designates the bonds that connect the two other parts of the molecule to the arylene or heteroarylene.

In particular, the arylenes and heteroarylenes described herein can connect the two parts of a molecule through bonds to two distinct positions on the arylene or heteroarylene. Examples of these types of connections include, for example:

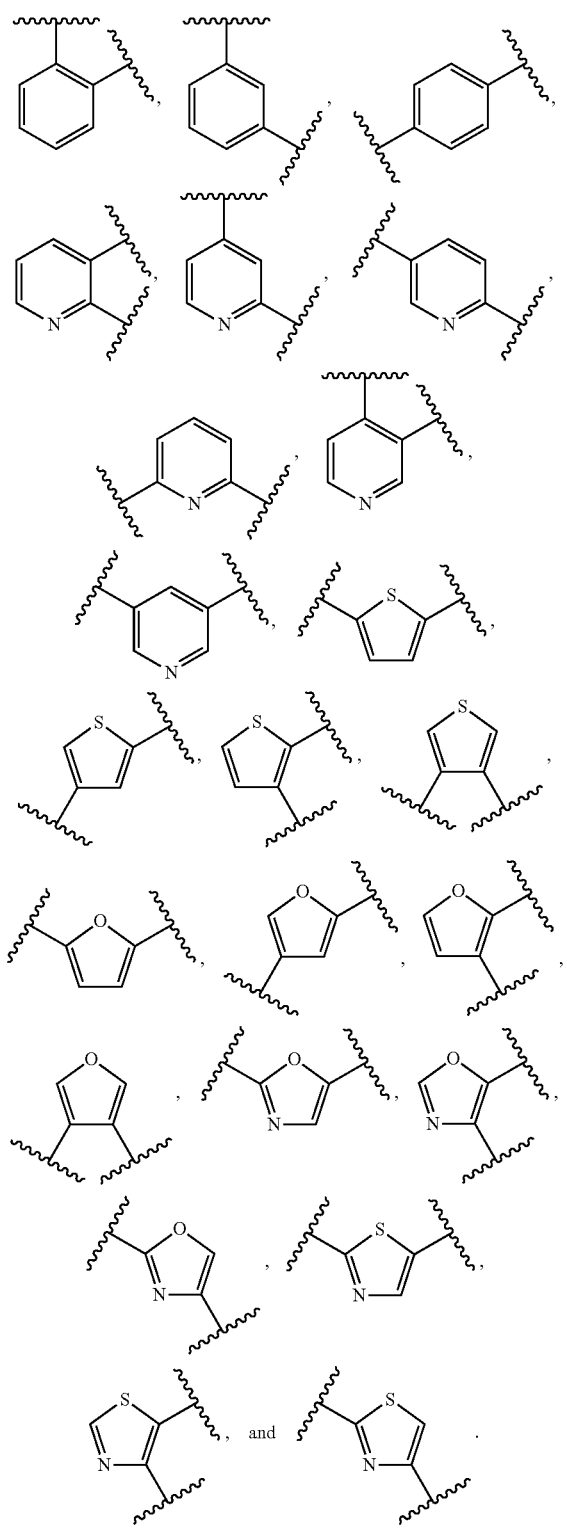

As used herein, "heterocyclic" refers to non-aromatic cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

As used herein, "halogen" or "halide" refers to fluoride, chloride, bromide or iodide. "Fluoride", "chloride", "bromide" or "iodide" can also be referred to as "fluoro", "chloro", "bromo", or "iodo", respectively.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers, and racemic mixtures as well as scalemic mixtures. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

A person of ordinary skill in the art understands the meaning of the stereochemistry associated with the hatched wedge/solid wedge structural features. For example, an introductory organic chemistry textbook (Francis A. Carey, Organic Chemistry, New York: McGraw-Hill Book Company 1987, p. 63) states "a wedge indicates a bond coming from the plane of the paper toward the viewer" and the hatched wedge "represents a bond receding from the viewer."

In particular, a skilled person will realize that even if the absolute stereochemistry of a particular stereoisomer (e.g. an enantiomer or diastereomer) of a molecule is not known, that particular stereoisomer can be distinguished from the other stereoisomers by use of other techniques (e.g. polarimetry, nuclear magnetic resonance spectroscopy, chromatography, and others identifiable to a skilled person). In particular, one exemplary method of distinguishing stereoisomers when the absolute stereochemistry of each stereoisomer is not known is chromatography such as high pressure liquid chromatography (HPLC). In particular, two or more stereoisomers such as diastereomers can be separated and characterized by their retention times, which would be expected to be replicable by using the same chromatographic conditions (e.g. flow rate, column material, solvent systems/gradient profiles, and others identifiable to a skilled person). In particular, a skilled person will realize that even when the exact relative retention times of one or more stereoisomers is not replicated (e.g. due to slight variations in the chromatographic parameters and/or chromatographic equipment), a stereoisomer with a shorter retention time can be said to be "faster eluting" and a stereoisomer with a linger retention time can be said to be "slower eluting". A skilled person will realize that once two or more stereoisomers are distinguished by a technique such as chromatography, the absolute stereochemistry of the stereoisomers can be determined by techniques or combinations of techniques identifiable to a skilled person (e.g. x-ray crystallography, vibrational circular dichroism, nuclear magnetic resonance, total synthesis, and others identifiable to a skilled person).

Some of the compounds of the invention may form salts with pharmaceutically acceptable acids or bases, and such pharmaceutically acceptable salts of the compounds described herein are also within the scope of the invention.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Exemplary ions include, for example, the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring. Salts can form from or incorporate one or more deprotonated acidic groups (e.g. carboxylic acids), one or more protonated basic groups (e.g. amines), or both (e.g. zwitterions).

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted.

Prodrug preparation is well known in the art. For example, "Prodrugs and Drug Delivery Systems," which is a chapter in Richard B. Silverman, *Organic Chemistry of Drug Design and Drug Action,* 2d Ed., Elsevier Academic Press: Amsterdam, 2004, pp. 496-557, provides further detail on the subject. In particular, alkyl esters having such as methyl, ethyl, isopropyl, and the like are contemplated. Also contemplated are prodrugs containing a polar group such as hydroxyl or morpholine. Examples of such prodrugs include compounds containing the moieties —CO$_2$(CH$_2$)$_2$OH, 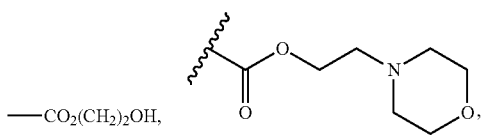

and the like.

The compounds of the invention are useful for reducing intraocular pressure. Reduction of intraocular pressure has been shown to delay or prevent the onset of primary open angle glaucoma, and to delay or prevent further vision loss in patients with primary open angle glaucoma. Thus, these compounds are also useful for treating glaucoma. Different types of suitable dosage forms and medicaments are well known in the art, and can be readily adapted for delivery of the compounds disclosed herein. For example, the compound could be dissolved or suspended in an aqueous solution or emulsion that is buffered to an appropriate pH, and administered topically to an eye of a mammal (see U.S. Pat. No. 7,091,231).

The terms "patient" and "subject" includes both human and animals. The term "mammal" means humans and other mammalian animals.

In some embodiments, the invention provides compounds having the structure:

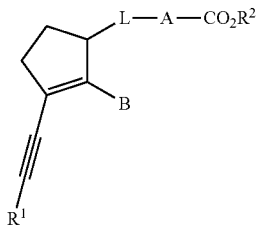

wherein:
L is C$_1$-C$_6$ alkylene;
A is arylene or heteroarylene;
B is substituted or unsubstituted aryl;
R$^1$ is H, C$_1$-C$_6$ alkyl, —CH$_2$OH, —CF$_3$, aryl, or heteroaryl; and
R$^2$ is H, C$_1$-C$_6$ alkyl, hydroxyethyl,

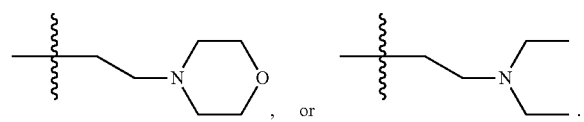

In some embodiments, L is C$_2$-C$_4$ alkylene.
In some embodiments, L is C$_3$ alkylene.
In some embodiments, A is phenylene, thiophenylene, furylene, pyridinylene, oxazolylene, or thiazolylene.
In some embodiments, A is thiophenylene.
In some embodiments, B is substituted phenyl.
In some embodiments, the substituent is 1-hydroxyhexyl.
In some embodiments, R$^1$ is —H, —CH$_2$OH, or phenyl.
In some embodiments, R$^2$ is —H.
In some embodiments, R$^2$ is C$_1$-C$_3$ alkyl.
In some embodiments, R$^2$ is isopropyl.

Exemplary compounds of the invention include, but are not limited to, compounds having any one of the following structures:

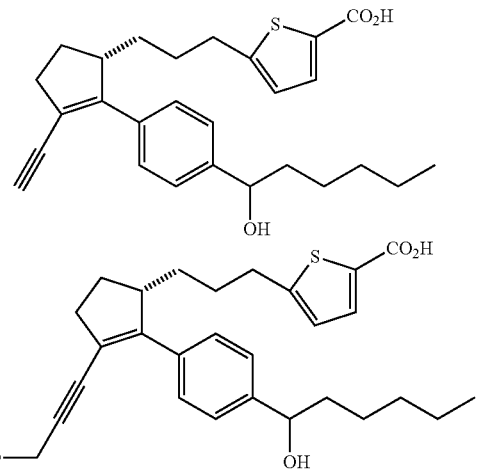

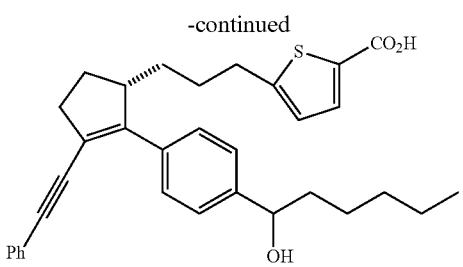

In other embodiments of the invention there are provided compositions including at least one compound according to the invention, wherein the composition is a liquid which is ophthalmically acceptable.

In other embodiments of the invention there are provided methods of treating glaucoma or ocular hypertension. Such methods can be performed, for example, by administering to a subject in need thereof a therapeutically effective amount of a compound of the invention. In certain embodiments the subject is human.

In other embodiments of the invention there are provided kits including a composition of the invention, a container, and instructions for administration of the composition to a subject in need thereof for the treatment of glaucoma or ocular hypertension.

For the purposes of this disclosure, "treat," "treating," or "treatment" refer to the use of a compound, composition, therapeutically active agent, or drug in the diagnosis, cure, mitigation, treatment, or prevention of disease or other undesirable condition.

Unless otherwise indicated, reference to a compound should be construed broadly to include pharmaceutically acceptable salts, prodrugs, tautomers, alternate solid forms, non-covalent complexes, and combinations thereof, of a chemical entity of a depicted structure or chemical name.

Tautomers are isomers that are in rapid equilibrium with one another. For example, tautomers may be related by transfer of a proton, hydrogen atom, or hydride ion. Unless stereochemistry is explicitly and unambiguously depicted, a structure is intended to include every possible stereoisomer, both pure or in any possible mixture.

Alternate solid forms are different solid forms than those that may result from practicing the procedures described herein. For example, alternate solid forms may be polymorphs, different kinds of amorphous solid forms, glasses, and the like.

Non-covalent complexes are complexes that may form between the compound and one or more additional chemical species that do not involve a covalent bonding interaction between the compound and the additional chemical species. They may or may not have a specific ratio between the compound and the additional chemical species. Examples might include solvates, hydrates, charge transfer complexes, and the like.

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they can be coated by known techniques to delay disintegration and absorption in the gastrointestinal tract and thereby provide a sustained action over a longer period. For example, a time delay material such as glyceryl monostearate or glyceryl distearate can be employed. They can also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds can be, in some embodiments, in the range of about 0.5 or about 1 to about 100 mg/kg/day.

A liquid which is ophthalmically acceptable is formulated such that it can be administered topically to the eye. The comfort can be maximized as much as possible, although sometimes formulation considerations (e.g. drug stability) may necessitate less than optimal comfort. In the case that comfort cannot be maximized, the liquid can be formulated such that the liquid is tolerable to the patient for topical ophthalmic use. Additionally, an ophthalmically acceptable liquid can either be packaged for single use, or contain a preservative to prevent contamination over multiple uses.

For ophthalmic application, solutions or medicaments are often prepared using a physiological saline solution as a major vehicle. Ophthalmic solutions can be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients can be used, for example, in the following amounts:

| Ingredient | Amount (% w/v) |
| --- | --- |
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

For the purposes of this disclosure, "treat," "treating," or "treatment" refer to the use of a compound, composition, therapeutically active agent, or drug in the diagnosis, cure, mitigation, treatment, prevention of disease or other undesirable condition, or to affect the structure or any function of the body of man or other animals.

The compounds disclosed herein are useful in the manufacture of a medicament for the treatment of glaucoma or ocular hypertension in a mammal.

Another embodiment is a medicament comprising a compound disclosed herein, wherein said composition is a liquid which is ophthalmically acceptable.

Another embodiment is a method comprising administering a compound disclosed herein to a mammal for the treatment of glaucoma or ocular hypertension.

Another embodiment is a kit comprising a composition comprising compound disclosed herein, a container, and instructions for administration of said composition to a mammal for the treatment of glaucoma or ocular hypertension.

EXAMPLES

The following examples are intended only to illustrate the invention and should in no way be construed as limiting the invention.

Synthetic Procedures

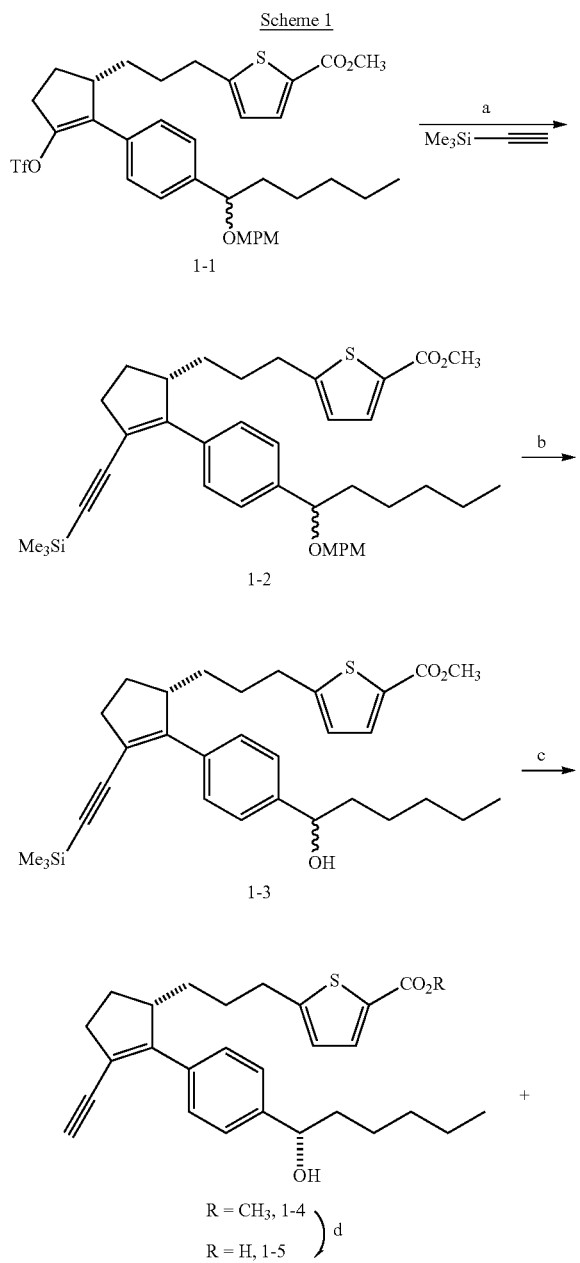

-continued

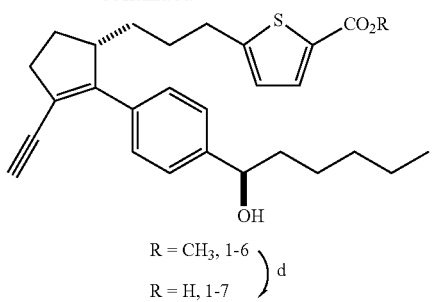

R = CH₃, 1-6
R = H, 1-7 } d

Conditions: (a) Pd[(Ph₃P)₂Cl₂], 2,6-lutidine, CuI, DMF 40° C.; (b) DDQ, CH₂Cl₂/H₂O; (c) TBAF, THF; HPLC separation; (d) 1M LiOH, THF, 60° C.

Scheme 2

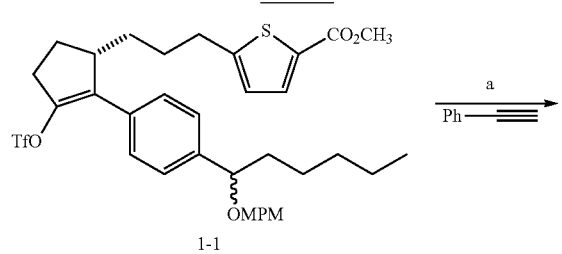

1-1

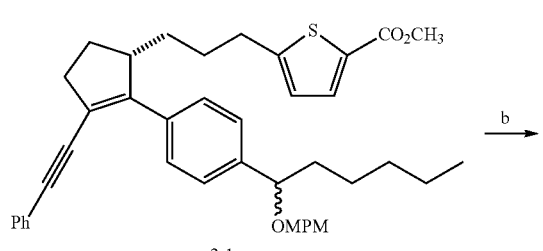

2-1

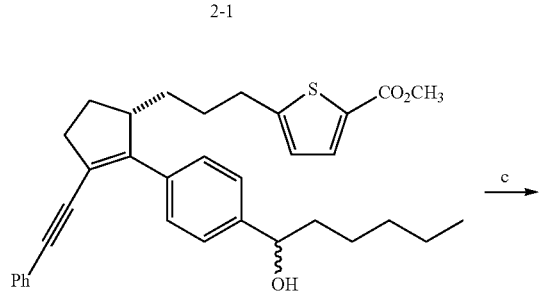

2-2

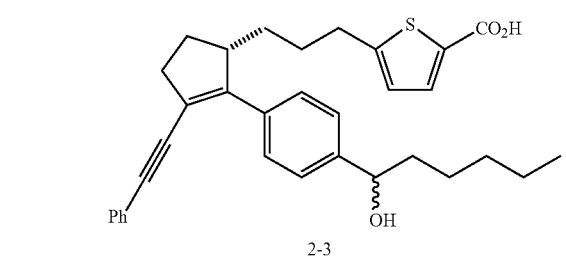

2-3

Conditions: (a) Pd[(Ph₃P)₂Cl₂], 2,6-lutidine, CuI, DMF 40° C.; (b) DDQ, CH₂Cl₂/H₂O; (c) 1M LiOH, THF, 60° C.

Scheme 3

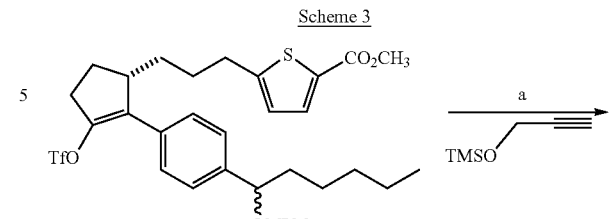

1-1

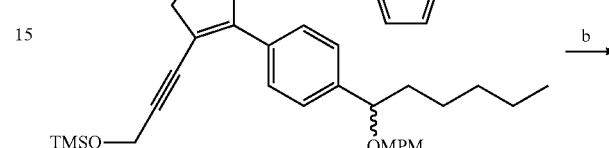

3-1

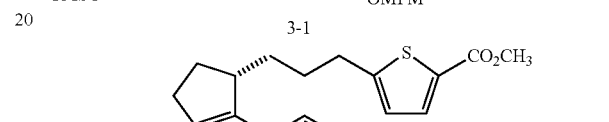

3-2

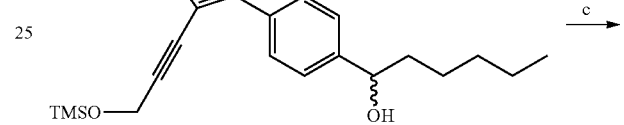

R = CH₃, 3-3
R = H, 3-4 } d

Conditions: (a) Pd[(Ph₃P)₂Cl₂], 2,6-lutidine, CuI, DMF 40° C.; (b) DDQ, CH₂Cl₂/H₂O; (c) TBAF, THF; (d) 1M LiOH, THF, 60° C.

methyl 5-(3-((1S)-2-(4-(1-((4-methoxybenzyl)oxy)hexyl)phenyl)-3-((trimethylsilyl)ethynyl)cyclopent-2-en-1-yl)propyl)thiophene-2-carboxylate (1-2)

CuI (36 mg, 0.19 mmol) was added to a mixture of 1-1 (532 mg, 0.77 mmol, U.S. patent application Ser. No. 12/524,305), (Ph₃P)₂PdCl₂ (27 mg, 0.04 mmol), and 2,6-lutidine (150 μL, 1.3 mmol) in DMF (0.6 mL). After 5 minutes at room temperature, the reaction was stirred at 40° C. for 3 h, and then was quenched by addition of 50 mL of saturated NH₄Cl solution. The resulting mixture was extracted with ethyl acetate (3×30 mL) and the combined ethyl acetate solution was washed with H₂O (30 mL) and brine (30 mL) and then was dried (Na₂SO₄), filtered and evaporated. The residue was purified by flash chromatography using a Combiflash unit from Teledyne Isco (0% ethyl acetate/hexanes→30%) to give the title compound (485 mg, 99%).

methyl 5-(3-((1S)-2-(4-(1-hydroxyhexyl)phenyl)-3-((trimethylsilyl)-ethynyl)cyclopent-2-en-1-yl)propyl)thiophene-2-carboxylate (1-3)

DDQ (160 mg, 0.71 mmol) was added to a solution of 1-2 (392 mg, 0.61 mmol) and H₂O (0.9 mL) in CH₂Cl₂ (18 mL).

After 30 minutes, saturated NaHCO$_3$ solution (40 mL) was added and the resulting mixture was extracted with CH$_2$Cl$_2$ (3×25 mL). The combined CH$_2$Cl$_2$ solution was washed with brine and then was dried (Na$_2$SO$_4$), filtered and evaporated. The residue was purified by flash chromatography using a Combiflash unit from Teledyne Isco (0% ethyl acetate/hexanes→40%) to give the title compound (66 mg, 21%).

Methyl 5-(3-((S)-3-ethynyl-2-(4-((S)-1-hydroxyhexyl)phenyl)cyclopent-2-en-1-yl)propyl)thiophene-2-carboxylate and 5-(3-((S)-3-ethynyl-2-(4-((R)-1-hydroxyhexyl)phenyl)cyclopent-2-en-1-yl)propyl)thiophene-2-carboxylate (1-4/1-6)

TBAF (0.40 mL, 0.40 mmol, 1 M/THF) was added to a solution of 1-3 (66 mg, 0.13 mmol) in 0.8 mL THF. After overnight stirring, the reaction was partitioned between 30 mL ethyl acetate and 20 mL brine. The organic layer was dried (Na$_2$SO$_4$), filtered and evaporated and the residue was purified by flash chromatography using a Combiflash unit from Teledyne Isco (0% ethyl acetate/hexanes 50%) to give the title compound (49 mg, 87%). The individual diastereomers could be separated by HPLC using a Lunar Phenomenex 50 mm×250 mm silica gel column (15% ethyl acetate/hexanes, 10 mg/0.5 mL/injection, 45 mL/min flow rate, 154 and 163 min. retention times for the two diastereomers).

5-(3-((S)-3-ethynyl-2-(4-((S)-1-hydroxyhexyl)phenyl)cyclopent-2-en-1-yl)propyl)thiophene-2-carboxylic acid and 5-(3-((S)-3-ethynyl-2-(4-((R)-1-hydroxyhexyl)phenyl)cyclopent-2-en-1-yl)propyl)thiophene-2-carboxylic acid (1-5/1-7)

The previously described LiOH procedure was used at 60° C. (see U.S. Pat. No. 7,091,231 B2).

5-(3-((1S)-2-(4-(1-hydroxyhexyl)phenyl)-3-(phenylethynyl)cyclopent-2-en-1-yl)propyl)thiophene-2-carboxylic acid (2-3)

The title compound was prepared using the sequence shown in scheme 2 with analogous procedures to those described above.

5-(3-((1S)-2-(4-(1-hydroxyhexyl)phenyl)-3-(3-hydroxyprop-1-yn-1-yl)cyclopent-2-en-1-yl)propyl)thiophene-2-carboxylic acid (3-4)

The title compound was prepared using the sequence shown in scheme 3 with analogous procedure to those described above.

A skilled person will realize that additional embodiments of the structure:

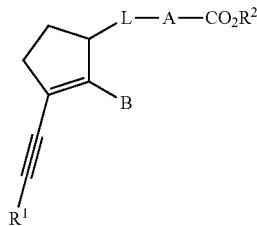

as described herein with L, A, R1, R2, and B groups different than those disclosed in the examples above can be made by techniques and reactions identifiable to a skilled person. In particular, a skilled person will realize that the appropriate starting material similar to compound 1-1, but comprising the chosen L, A, R2 and B groups different than those disclosed in the examples above, can by synthesized using the reactions and corresponding appropriate starting materials shown in, for example, U.S. patent application Ser. No. 12/524,305 and references described therein (e.g. U.S. Provisional Applications 60/744,236; 60/742,779, and 60/746,386, and U.S. patent application Ser. No. 11/009,298).

BIOLOGICAL DATA

Binding Data $K_i$

Competition binding experiments were performed in a medium containing Hank's balanced salt solution, Hepes 20 mM, pH 7.3, membranes (~60 µs protein) or 2×10$^5$ cells from HEK 293 cells stably expressing human EP$_2$ receptors, [$^3$H] PGE2 (10 nM) and various concentrations of test compounds in a total volume of 300 µl. Reaction mixtures were incubated at 23° C. for 60 min, and were filtered over Whatman GF IB filters under vacuum. Filters were washed three times with 5 ml ice-cold buffer containing 50 mM Tris/HCl (PH 7.3). Non-specific binding was estimated in the presence of excess unlabeled PGE2 (10 µM). Binding data fitted to the binding model for a single class of binding sites, using nonlinear regression analysis. IC$_{50}$ values thus obtained were converted to $K_i$ using the equation of $K_i=(IC_{50}/(1+[L]/K_D))$ where [L] represents PGE2 concentration (10 nM) and $K_D$ the dissociation constant for [$^3$H]PGE2 at human EP$_2$ receptors (40 nM).

Radioligand Binding

Cells Stably Expressing EP$_1$, EP$_2$, EP$_4$, and FP Receptors

HEK-293 cells stably expressing the human or feline FP receptor, or EP$_1$, EP$_2$, or EP$_4$ receptors were washed with TME buffer, scraped from the bottom of the flasks, and homogenized for 30 sec using a Brinkman PT 10/35 polytron. TME buffer was added to achieve a final 40 ml volume in the centrifuge tubes (the composition of TME is 100 mM TRIS base, 20 mM MgCl$_2$, 2M EDTA; ION HCl is added to achieve a pH of 7.4).

The cell homogenate was centrifuged at 19000 rpm for 20 min at 4° C. using a Beckman Ti-60 rotor. The resultant pellet was resuspended in TME buffer to give a final 1 mg/ml protein concentration, as determined by Biorad assay. Radioligand binding competition assays vs. [$^3$H-]17-phenyl PGF$_{2\alpha}$ (5 nM) were performed in a 100 µl volume for 60 min. Binding reactions were started by adding plasma membrane fraction. The reaction was terminated by the addition of 4 ml ice-cold TRIS-HCl buffer and rapid filtration through glass fiber GF/B filters using a Brandel cell harvester. The filters were washed 3 times with ice-cold buffer and oven dried for one hour.

[$^3$H-] PGE$_2$ (specific activity 180 Ci mmol) was used as the radio ligand for EP receptors. [$^3$H] 17-phenyl PGF$_{2\alpha}$ was employed for FP receptor binding studies. Binding studies employing EP$_1$, EP$_2$, EP$_4$ and FP receptors were performed in duplicate in at least three separate experiments. A 200 µl assay volume was used. Incubations were for 60 min at 25° C. and were terminated by the addition of 4 ml of ice-cold 50 mM TRIS-HCl, followed by rapid filtration through Whatman GF/B filters and three additional 4 ml washes in a cell harvester (Brandel). Competition studies were performed using a final concentration of 5 nM [$^3$H]-PGE$_2$, or 5 nM [$^3$H] 17-phenyl PGF$_{2\alpha}$ and non-specific binding determined with 10$^{-5}$ M of unlabeled PGE$_2$, or 17-phenyl PGF$_{2\alpha}$ according to receptor subtype studied.

Methods for FLIPR™ Studies (a) Cell Culture

HEK-293(EBNA) cells, stably expressing one type or subtype of recombinant human prostaglandin receptors (prostaglandin receptors expressed: hDP/Gqs5; $hEP_1$, $hEP_2$/Gqs5; $hEP_{3A}$/Gqi5; $hEP_4$/Gqs5; hFP; hIP; hTP), were cultured in 100 mm culture dishes in high-glucose DMEM medium containing 10% fetal bovine serum, 2 mM I-glutamine, 250 μg/ml geneticin (G418) and 200 μg/ml hygromycin B as selection markers, and 100 units/ml penicillin G, 100 μg/ml streptomycin and 0.25 μg/ml amphotericin B.

(b) Calcium Signal Studies on the FLIPR™

Cells were seeded at a density of $5 \times 10^4$ cells per well in Biocoat® Poly-D-lysine-coated black-wall, clear-bottom 96-well plates (Becton-Dickinson) and allowed to attach overnight in an incubator at 37° C. Cells were then washed two times with HBSS-HEPES buffer (Hanks Balanced Salt Solution without bicarbonate and phenol red, 20 mM HEPES, pH 7.4) using a Denley Cellwash plate washer (Labsystems). After 45 minutes of dye-loading in the dark, using the calcium-sensitive dye Fluo-4 AM at a final concentration of 2 μM, plates were washed four times with HBSS-HEPES buffer to remove excess dye leaving 100 μl, in each well. Plates were re-equilibrated to 37° C. for a few minutes.

Cells were excited with an Argon laser at 488 nm, and emission was measured through a 510-570 nm bandwidth emission filter (FLIPR™, Molecular Devices, Sunnyvale, Calif.). Drug solution was added in a 50 μL volume to each well to give the desired final concentration. The peak increase in fluorescence intensity was recorded for each well. On each plate, four wells each served as negative (HBSS-HEPES buffer) and positive controls (standard agonists: BW245C (hDP); $PGE_2$($hEP_1$, $hEP_2$/Gqs5; $hEP_{3A}$/Gqi5; $hEP_4$/Gqs5); $PGF_{2\alpha}$ (hFP); carbacyclin (hIP); U-46619 (hTP), depending on receptor). The peak fluorescence change in each drug-containing well was then expressed relative to the controls.

Compounds were tested in a high-throughput (HTS) or concentration-response (CoRe) format. In the HTS format, forty-four compounds per plate were examined in duplicates at a concentration of $10^{-5}$ M. To generate concentration-response curves, four compounds per plate were tested in duplicates in a concentration range between $10^{-5}$ and $10^{-11}$. The duplicate values were averaged. In either, HTS or CoRe format each compound was tested on at least 3 separate plates using cells from different passages to give an n≥3.

TABLE 1

| entry | STRUCTURE | EP2 cAMP EC50 (nM) | EP2 Ki (nM) | EP2 Ca2+ EC50 (nM) | EP4 Ki EC50 (nM) | EP4 Ca2+ EC50 (nM) | OTHER RECEPTORS Ca2+ EC50 (nM) |
|---|---|---|---|---|---|---|---|
| 1 | 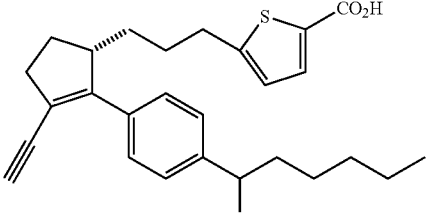 slower eluting diasteromer | 0.2 | 2 | 48 | 2821 | >10K | DP(7734), EP3(171) NA: EP1, TP |
| 2 | 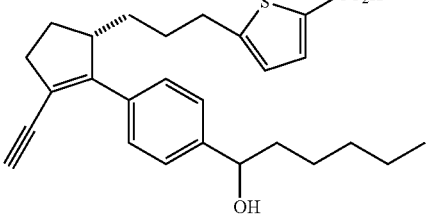 faster eluting diasteromer | 0.2 | 7 | 22 | 712 | >10K | DP(>10K), EP3(1544) NA: EP1, FP, IP, TP |
| 3 | 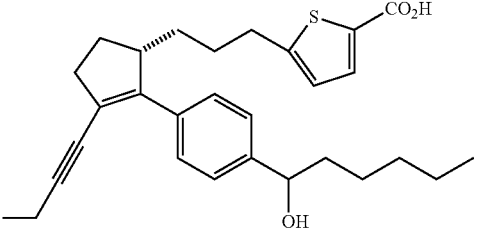 | 1.5 | 17 | 0.5 | 783 | >10K | DP(220), EP3(7403) NA: EP1, FP, IP, TP |

TABLE 1-continued

| | | EP2 | | | EP4 | | |
|---|---|---|---|---|---|---|---|
| entry | STRUCTURE | cAMP EC50 (nM) | Ki (nM) | Ca2+ EC50 (nM) | Ki EC50 (nM) | Ca2+ EC50 (nM) | OTHER RECEPTORS Ca2+ EC50 (nM) |
| 4 | 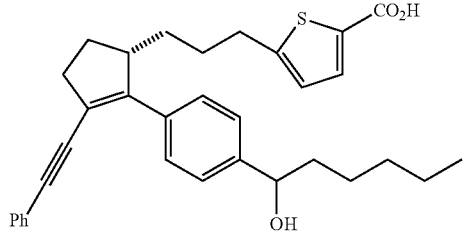 [SMILES: CCCCCC(O)c1ccc(C2=C(C#Cc3ccccc3)CC[C@@H]2CCCc2ccc(C(=O)O)s2)cc1] | 140 | 2527 | 513 | 8195 | >10K | EP3(7079) NA: DP, EP1, FP, IP, TP | cAMP Assay

A 384-well drug plate was prepared to contain 6 test compounds, $PGE_2$ and cAMP in 16 serial dilutions in triplicate, using a Biomek station. HEK-EBNA cells expressing a target PG receptor subtype ($EP_2$ or $EP_4$) were suspended in a stimulation buffer (HBSS, 0.1% BSA, 0.5 mM IBMX and 5 mM HEPES, pH 7.4) in a density of $10^4$ cells/5 µL. The reaction was initiated by mixing 5 µL drug dilutions with 5 µL of HEK-EBNA cells in a well, carried out for 30 min at room temperature, and followed by the addition of 5 µL anti-cAMP acceptor beads in the control buffer with Tween-20 (25 mM NaCl, 0.03% Tween-20, 5 mM HEPES, pH 7.4). After 30 min in the dark at room temperature, the mixtures were incubated with 15 µL biotinylated-cAMP/strepavidin donor beads in Lysis/Detection buffer (0.1% BSA, 0.3% Tween-20 and 5 mM HEPES, pH 7.4) for 45 min at the room temperature. Fluorescence changes were read using a Fusion-alpha HT microplate reader.

The results of the binding and activity studies, presented in Table 1 herein, demonstrate that the compounds disclosed herein are selective prostaglandin $EP_2$ agonists, and are thus useful for the treatment of glaucoma, ocular hypertension, the other diseases or conditions disclosed herein.

In Vivo Testing
Intraocular Pressure (10P)

Intraocular pressure studies in dogs involved pneumatonometry performed in conscious, Beagle dogs of both sexes (10-15 kg). The animals remained conscious throughout the study and were gently restrained by hand. Drugs were administered topically to one eye as a 25 µL volume drop, the other eye received 25 µl, vehicle (0.1% polysorbate 80: 10 mM TRIS) as a control. Proparacaine (0.1%) was used for corneal anesthesia during tonometry. Intraocular pressure was determined just before drug administration and at 2, 4 and 6 hr thereafter on each day of the 5 day study. Drug was administered immediately after the first 10P reading.

Ocular Surface Hyperemia

Ocular surface hyperemia was visually assessed and scored according to a system typically used clinically.

| Hyperimia Score | Assigned Value |
|---|---|
| <1 trace | 0.5 |
| 1 mild | 1 |
| moderate | 2 |
| severe | 3 |

Ocular surface hyperemia was evaluated at the same time points as intraocular pressure measurement. It should be noted that untreated dog eyes frequently have a pink/red tone. Thus, values of trace or even mild are not necessarily out of the normal range. Similar tests were used to determine ocular surface hyperemia on monkeys.

The results of the in vivo studies, are presented in Table 2 herein.

TABLE 2

| | | | DOG | | MONKEY |
|---|---|---|---|---|---|
| ENTRY | STRUCTURE | Conc. (g/100 mL) | Max. ΔIOP (%) | Max. hyperemia | Max. ΔIOP (%) |
| 1 | 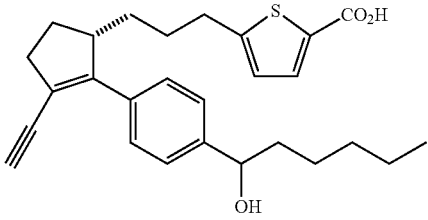<br>Slower eluting diastereomer | 0.003% | −40 | 1.5 | −45 |

TABLE 2-continued

| | | | DOG | | MONKEY |
| ENTRY | STRUCTURE | Conc. (g/100 mL) | Max. ΔIOP (%) | Max. hyperemia | Max. ΔIOP (%) |
| --- | --- | --- | --- | --- | --- |
| 2 | 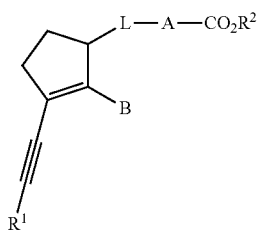 Faster eluting diastereomer | 0.003% | −37 | 2 | −30 |

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the claims.

Throughout this specification reference is made to publications such as US and foreign patent applications, journal articles, book chapters, and others. All such publications are expressly incorporated by reference in their entirety, including supplemental/supporting information sections published with the corresponding references, for all purposes unless otherwise indicated.

The foregoing descriptions details specific methods and compositions that can be employed to practice the present invention, and represents the best mode contemplated. It should not be construed as limiting the overall scope hereof; rather, the ambit of the present invention is to be governed only by the lawful construction of the appended claims.

What is claimed is:

1. A compound having the structure:

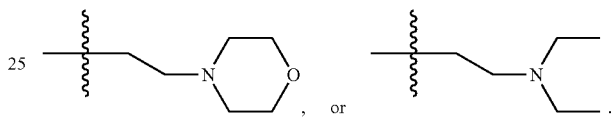

or a pharmaceutically acceptable salt thereof, wherein:
L is $C_1$-$C_6$ alkylene;
A is arylene or heteroarylene;
B is substituted or unsubstituted aryl;
$R^1$ is H, $C_1$-$C_6$ alkyl, —$CH_2OH$, —$CF_3$, aryl, or heteroaryl; and $R^2$ is H, $C_1$-$C_6$ alkyl, hydroxyethyl,

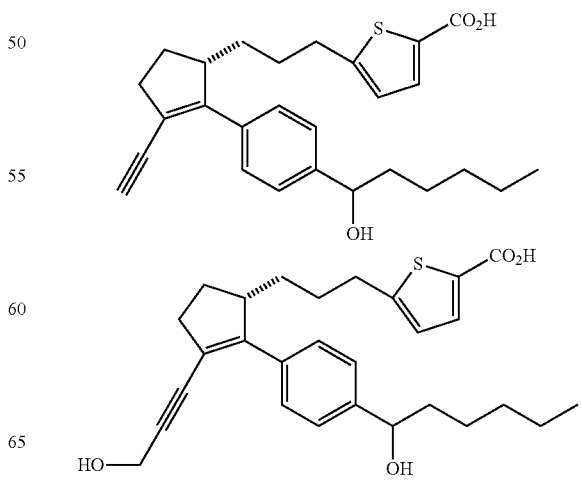, or

2. The compound of claim 1, wherein L is $C_2$-$C_4$ alkylene.
3. The compound of claim 1, wherein L is $C_3$ alkylene.
4. The compound of claim 1, wherein A is phenylene, thiophenylene, furylene, pyridinylene, oxazolylene, or thiazolylene.
5. The compound of claim 4, wherein A is thiophenylene.
6. The compound of claim 1, wherein B is substituted phenyl.
7. The compound of claim 6, wherein the substituent is 1-hydroxyhexyl.
8. The compound of claim 1, wherein $R^1$ is —H, —$CH_2OH$, or phenyl.
9. The compound of claim 1, wherein $R^2$ is —H.
10. The compound of claim 1, wherein $R^2$ is $C_1$-$C_3$ alkyl.
11. The compound of claim 1, wherein $R^2$ is isopropyl.
12. The compound of claim 1 having any one of the following structures:

-continued

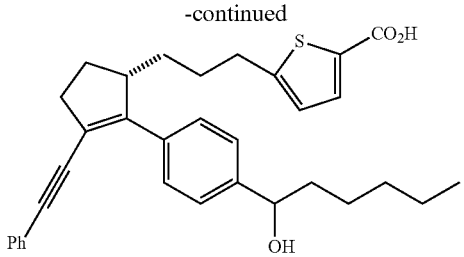

or being a pharmaceutically acceptable salt of any one of said structures.

13. A composition comprising at least one compound according to claim 1, or a pharmaceutically acceptable salt thereof, and at least one pharmaceutically acceptable excipient.

14. A method of treating glaucoma or ocular hypertension comprising administering to a subject in need thereof a compound according to claim 1 or a pharmaceutically acceptable salt thereof.

15. The method of claim 14 wherein the subject is human.

16. A kit comprising the composition of claim 13, a container, and instructions for administration of the composition to a subject in need thereof for the treatment of glaucoma or ocular hypertension.

* * * * *